(12) United States Patent
Nishino et al.

(10) Patent No.: US 8,330,597 B2
(45) Date of Patent: Dec. 11, 2012

(54) RADIATION DETECTION APPARATUS AND RADIATION IMAGE CAPTURING SYSTEM

(75) Inventors: Naoyuki Nishino, Minami-ashigara (JP); Eiichi Kito, Minami-ashigara (JP); Yasunori Ohta, Yokohama (JP); Hiroshi Tamaoki, Odawara (JP); Tatsuo Iiyama, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 959 days.

(21) Appl. No.: 12/320,476

(22) Filed: Jan. 27, 2009

(65) Prior Publication Data

US 2009/0189761 A1 Jul. 30, 2009

(30) Foreign Application Priority Data

Jan. 28, 2008 (JP) ................. 2008-016826

(51) Int. Cl.
 *G08B 21/00* (2006.01)
 *H05G 1/54* (2006.01)
 *G01T 1/24* (2006.01)
(52) U.S. Cl. ............... 340/540; 378/117; 250/370.01
(58) Field of Classification Search .......... 340/540; 378/117; 250/370.01
 See application file for complete search history.

(56) References Cited

U.S. PATENT DOCUMENTS

| | | | | |
|---|---|---|---|---|
| 7,046,764 | B1* | 5/2006 | Kump | 378/117 |
| 7,581,884 | B1* | 9/2009 | Barnes et al. | 378/205 |
| 7,638,773 | B2* | 12/2009 | Kuwabara et al. | 250/370.08 |
| 8,031,837 | B2* | 10/2011 | Spahn | 378/91 |
| D656,614 | S* | 3/2012 | Stinson | D24/161 |
| 2004/0164252 | A1* | 8/2004 | Yonekawa | 250/484.4 |
| 2006/0054829 | A1* | 3/2006 | Tsuchino et al. | 250/370.09 |
| 2006/0093089 | A1* | 5/2006 | Vertatschitsch et al. | 378/65 |
| 2006/0202127 | A1* | 9/2006 | Ozeki | 250/370.01 |
| 2007/0213654 | A1* | 9/2007 | Lundtveit et al. | 604/29 |
| 2008/0312501 | A1* | 12/2008 | Hasegawa et al. | 600/117 |
| 2009/0209852 | A1* | 8/2009 | Mate et al. | 600/431 |
| 2009/0232278 | A1 | 9/2009 | Ohara | |
| 2011/0178359 | A1* | 7/2011 | Hirschman et al. | 600/4 |
| 2011/0233411 | A1* | 9/2011 | Nishino et al. | 250/361 R |

FOREIGN PATENT DOCUMENTS

| | | |
|---|---|---|
| JP | 59-168176 | 11/1984 |
| JP | 3494683 | 6/1995 |
| JP | 2000-105297 | 4/2000 |
| JP | 2004-101195 | 4/2004 |
| JP | 2004-173908 | 6/2004 |
| JP | 2005-173432 | 6/2005 |
| WO | WO 2006/080377 | 8/2006 |

* cited by examiner

*Primary Examiner* — George Bugg
*Assistant Examiner* — Jack K Wang
(74) *Attorney, Agent, or Firm* — Jean C. Edwards, Esq.; Edwards Neils

(57) ABSTRACT

A radiation detection apparatus and a radiation image capturing system according to the present invention includes an electronic cassette equipped with a casing, and a radiation detection device accommodated inside the casing, which detects radiation emitted from a radiation source and having passed through a subject, while converting the radiation into radiation image information. The electronic cassette includes a sensor for sensing that the casing has been lifted, a power supply controller for supplying power based on a detection signal from the sensor, a discriminating unit for discriminating whether the radiation detection apparatus has transitioned to an image capturing capable mode, and a warning signal output unit for outputting a warning signal, for issuing a warning when the radiation detection apparatus cannot transition to the image capturing capable mode.

22 Claims, 8 Drawing Sheets

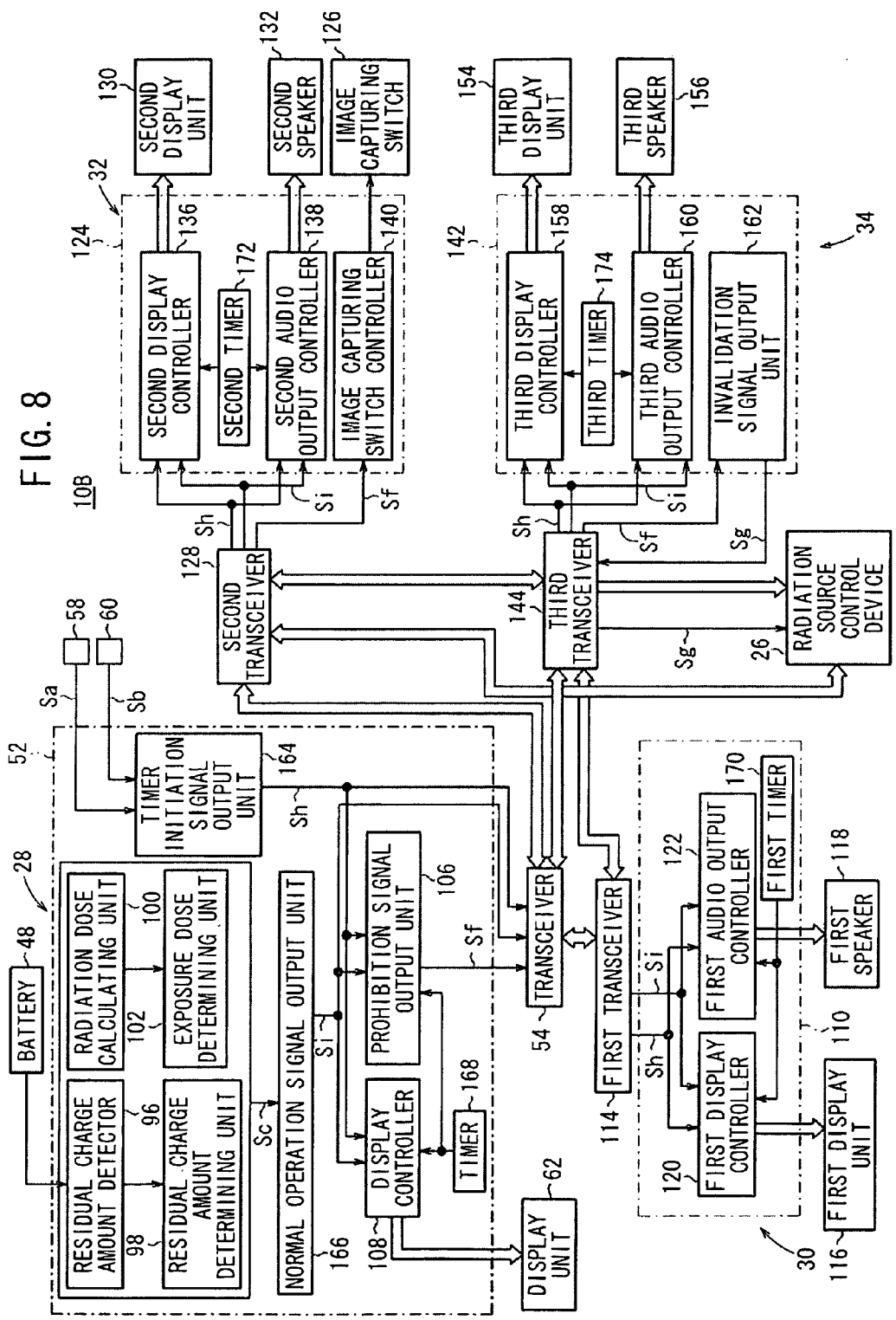

RADIATION DETECTION APPARATUS AND RADIATION IMAGE CAPTURING SYSTEM

CROSS-REFERENCE TO RELATED APPLICATIONS

The present application claims priority from Japanese Patent Application No. 2008-016826, filed Jan. 28, 2008, the contents of which are herein incorporated by reference in their entirety.

BACKGROUND OF THE INVENTION

1. Field of the Invention

The present invention relates to a radiation detection apparatus for irradiating a subject with radiation and capturing a radiation image, and to a radiation image capturing system that uses such a radiation detection apparatus.

2. Description of the Related Art

In the medical field, a radiation image capturing apparatus, in which radiation is applied to a subject, and radiation that has passed through the subject is directed to a radiation detection device for capturing a radiation image of the subject, has been widely used.

In this case, as types of radiation detection devices, there are known a conventional radiation film on which a radiation image is exposed and recorded, or a stimulable phosphor panel in which radiation energy is stored as a radiation image in a stimulable phosphor body, and when stimulating light is applied thereto, the radiation image can be read out as stimulated light. In such radiation detection devices, the radiation film in which a radiation image has been recorded is supplied to a developing apparatus where an image developing process is carried out, or the stimulable phosphor panel is supplied to a reading apparatus in which the radiation image is acquired as a visible image by performing a reading process thereon.

On the other hand, in a medical environment such as an operating room or the like, for performing rapid and precise treatments with respect to a patient, it is essential to read out and display the radiation image directly from the radiation detection device. As a radiation detection device capable of responding to such requirements, a radiation detection device has been developed that uses solid state detection elements, which convert radiation directly into electrical signals, or which, after the radiation has been converted into visible light by a scintillator, convert the visible light into electrical signals, which are read out.

In particular, in a transportable type of device, a battery for supplying electrical power to the radiation detection device and to various electronic circuits is accommodated inside of a casing in which the radiation detection device is housed. Generally, such a transportable device is referred to as an electronic cassette. In this type of electronic cassette, naturally, it is desirable to reduce the electrical power consumption of the battery.

In the aforementioned transportable type of electronic cassette in which a battery is accommodated, for example, as one method for reducing power consumption of the battery, the method disclosed in Japanese Laid-Open Patent Publication No. 2005-173432 has been proposed.

This method has the object of avoiding needless power consumption corresponding to the operative condition of the radiation cassette itself, and is equipped with a contact sensing unit and/or an orientation detection sensor (angle sensor, vibration gyro or the like) in a portion of the casing of the electronic cassette. In addition, during the time that contact is detected, the power supply is suppressed, and when contact with the electronic cassette is not sensed, an image capturing capable mode is enabled.

However, in the method disclosed in Japanese Laid-Open Patent Publication No. 2005-173432, since it is not known until the electronic cassette is set at a desired position, whether or not the electronic cassette is actually capable of capturing an image, and thus, there is a problem in that time may be required in order to replace the electronic cassette with a different electronic cassette.

SUMMARY OF THE INVENTION

The present invention, taking into consideration the above-mentioned problems, has the object of providing a radiation detection apparatus and a radiation image capturing system, which enables image capturing to be performed by transition to an image capturing capable mode at a stage when the radiation detection device is carried by a technician, so that the time from when the radiation detection device is set at a desired position until capturing of the radiation image is started can be shortened.

Herein, the term "transition to an image capturing capable mode" is assumed to imply a case in which the radiation detection device can transition completely to an image capturing capable mode.

Further, another object of the present invention is to provide a radiation detection apparatus and a radiation image capturing system, in which, by issuing a warning in the case that the radiation detection apparatus cannot transition to an image capturing capable mode during a stage when a technician is carrying the radiation detection device, the time for switching to another radiation detection device can be shortened.

Further, yet another object of the present invention is to provide a radiation detection apparatus and a radiation image capturing system, in which exposure is prohibited and thus needless exposure can be prevented in the case that the radiation detection apparatus cannot transition to an image capturing capable mode during a stage when a technician is carrying the radiation detection apparatus.

A radiation detection apparatus according to a first aspect of the present invention includes a casing and a radiation detection device accommodated inside the casing, which detects radiation emitted from a radiation source and having passed through a subject, and converts the radiation into radiation image information. The invention further includes a sensor for sensing that the casing has been lifted, a power supply controller for supplying power based on a detection signal from the sensor, a discriminating unit for discriminating whether the radiation detection apparatus has transitioned to an image capturing capable mode, and a warning signal output unit for outputting a warning signal and thereby issuing a warning in the event that the radiation detection apparatus cannot transition to the image capturing capable mode.

A radiation detection apparatus according to a second aspect of the present invention includes a casing and a radiation detection device accommodated inside the casing, which detects radiation emitted from a radiation source and having passed through a subject, and converts the radiation into radiation image information. The invention further includes a sensor for sensing that the casing has been lifted, a power supply controller for supplying power based on a detection signal from the sensor, a discriminating unit for discriminating whether the radiation detection apparatus has transitioned to an image capturing capable mode, and a normal operation signal output unit for outputting a normal operation signal indicating that the radiation detection apparatus has transitioned to the image capturing capable mode when the radiation detection apparatus has transitioned to the image capturing capable mode.

According to a third aspect of the present invention, a radiation image capturing system is provided with a radiation detection apparatus including a casing, a radiation detection device accommodated inside the casing, which detects radiation emitted from a radiation source and having passed through a subject, and converts the radiation into radiation image information, and a battery. The invention further includes a cradle for carrying out charging with respect to at least the battery by mounting the radiation detection apparatus into the cradle. The radiation detection apparatus comprises a sensor for sensing that the casing has been lifted, a power supply controller for supplying power based on a detection signal from the sensor, a discriminating unit for discriminating whether the radiation detection apparatus has transitioned to an image capturing capable mode, and a warning signal output unit for outputting a warning signal, for issuing a warning in the event that the radiation detection apparatus cannot transition to the image capturing capable mode. Further, the cradle comprises a warning output unit for issuing a warning based on input of the warning signal output from the warning signal output unit of the radiation detection apparatus.

According to a fourth aspect of the present invention, a radiation image capturing system is provided with a radiation detection apparatus including a casing, a radiation detection device accommodated inside the casing, which detects radiation emitted from a radiation source and having passed through a subject, and converts the radiation into radiation image information, and a battery. The invention further includes a cradle for carrying out charging with respect to at least the battery by mounting the radiation detection apparatus into the cradle. The radiation detection apparatus comprises a sensor for sensing that the casing has been lifted, a power supply controller for supplying power based on a detection signal from the sensor, a discriminating unit for discriminating whether the radiation detection apparatus has transitioned to an image capturing capable mode, and a normal operation signal output unit for outputting a normal operation signal indicating that the radiation detection apparatus has transitioned to the image capturing capable mode when the radiation detection apparatus has transitioned to the image capturing capable mode. Further, the cradle comprises a warning output unit for issuing a warning in the case that the normal operation signal has not been input from the normal operation signal output unit even after a predetermined time period has elapsed from output of the detection signal from the sensor.

According to a fifth aspect of the present invention, a radiation image capturing system is provided with a radiation detection apparatus including a casing, and a radiation detection device accommodated inside the casing, which detects radiation having passed through a subject, and converts the radiation into radiation image information. The invention further includes an image capturing apparatus for irradiating the subject with radiation, and a controller for controlling at least the image capturing apparatus by carrying out exchange of information with the radiation detection apparatus. The radiation detection apparatus comprises a sensor for sensing that the casing has been lifted, a power supply controller for supplying power based on a detection signal from the sensor, a discriminating unit for discriminating whether the radiation detection apparatus has transitioned to an image capturing capable mode, and a warning signal output unit for outputting a warning signal, for issuing a warning in the event that the radiation detection apparatus cannot transition to the image capturing capable mode. Also, the controller comprises a warning output unit for issuing a warning based on input of the warning signal output from the warning signal output unit of the radiation detection apparatus.

According to a sixth aspect of the present invention, a radiation image capturing system is provided with a radiation detection apparatus including a casing, a radiation detection device accommodated inside the casing, which detects radiation having passed through a subject, and converts the radiation into radiation image information. The invention further includes an image capturing apparatus for irradiating the subject with radiation, and a controller for controlling at least the image capturing apparatus by carrying out exchange of information with the radiation detection apparatus. The radiation detection apparatus comprises a sensor for sensing that the casing has been lifted, a power supply controller for supplying power at least to the radiation detection device based on a detection signal from the sensor, a discriminating unit for discriminating whether the radiation detection apparatus has transitioned to an image capturing capable mode, and a normal operation signal output unit for outputting a normal operation signal indicating that the radiation detection apparatus has transitioned to the image capturing capable mode, when the radiation detection apparatus has transitioned to the image capturing capable mode. Also, the controller comprises a warning output unit for issuing a warning in the case that the normal operation signal has not been input from the normal operation signal output unit even after a predetermined time period has elapsed from output of the detection signal from the sensor.

The following advantages and effects are offered in accordance with the present invention:

(1) By transition to an image capturing capable mode at a stage when the radiation detection apparatus is lifted by a technician, an image capturing capable condition is available at any time, the time from when the radiation detection apparatus is set at a desired position to when image capturing is initiated can be shortened.

(2) By issuing a warning in the event that the radiation detection apparatus cannot transition to the image capturing capable mode at a stage when the radiation detection apparatus is lifted by a technician, the time required for replacing the radiation detection apparatus with a different radiation detection apparatus can be shorted.

(3) In the case that the radiation detection apparatus cannot transition to the image capturing capable mode at a stage when the radiation detection apparatus is lifted by a technician, exposure is prohibited and thus needles exposures can be avoided.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 8 is a schematic block diagram showing main components of each of the controllers of a second radiation image capturing system.

DESCRIPTION OF THE PREFERRED EMBODIMENTS

Below, a description shall be provided with reference to FIGS. 1 through 8 of embodiments of a radiation detection apparatus and radiation image capturing system according to the present invention.

Figure 1:
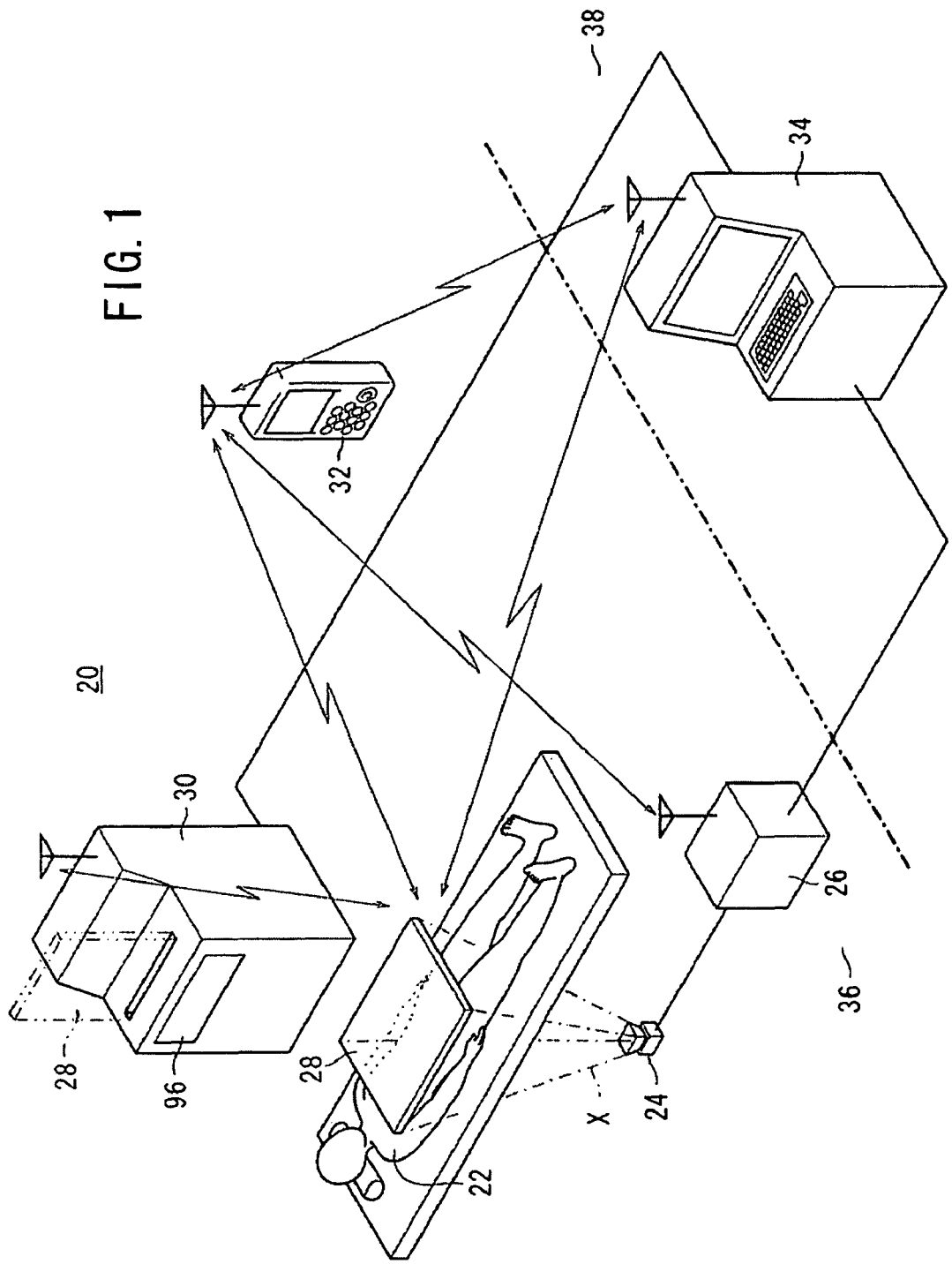
FIG. 1 is a schematic view showing a first radiation image capturing system according to an embodiment of the present invention.

As shown in FIG. 1, a radiation image capturing system according to a first embodiment (hereinafter referred to as a first radiation image capturing system 10A) includes a radiation source 24 for irradiating a patient 22 (subject) with radiation X having a given dose according to image capturing conditions, a radiation source control device 26 for controlling the radiation source 24, a radiation detection apparatus (hereinafter referred to as an electronic cassette 28) having a radiation detection device therein for detecting radiation X that has passed through the patient 22, a cradle 30 for carrying out a charging process with respect to the electronic cassette 28, a portable information terminal 32 having an image capturing switch for the radiation source 24, and which is carried by a technician for confirming conditions including image capturing operations, and a console 34 (controller), by which the radiation source control device 26, the electronic cassette 28, the cradle 30 and the portable information terminal 32 are controlled, while also transmitting and receiving necessary information therebetween.

The radiation source 24, the radiation source control device 26, and the cradle 30 are arranged inside of an image capturing room 36 where the image is to be captured, whereas the console 34 is disposed in an operations room 38 outside of the image capturing room 36. Further, transmission and reception of necessary information are carried out between the radiation source control device 26, the electronic cassette 28, the cradle 30, the portable information terminal 32 and the console 34, by means of wireless communications.

Figure 2:
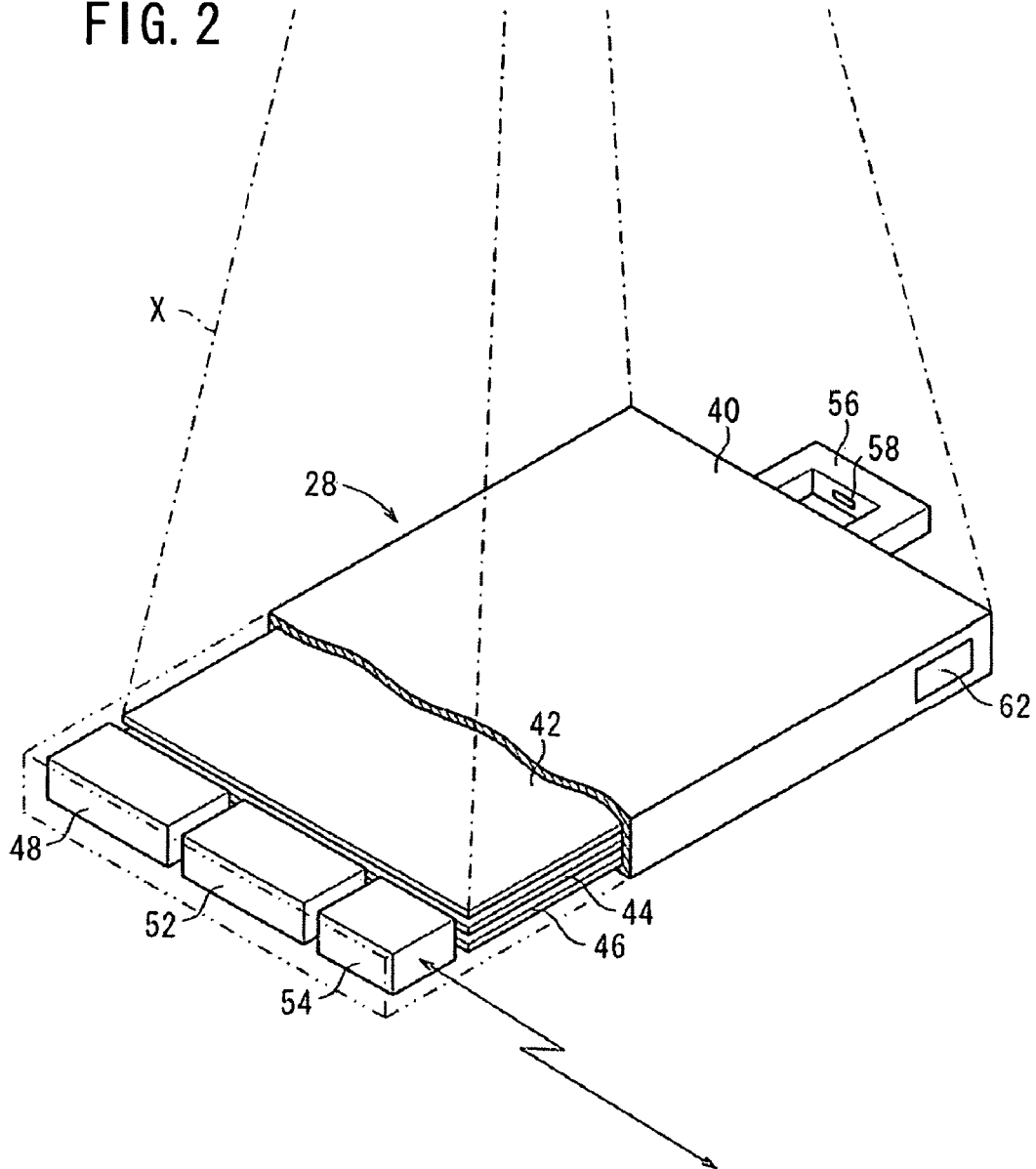
FIG. 2 is an interior structural view of an electronic cassette.

As shown in FIG. 2, the electronic cassette 28 is equipped with a casing 40 made from a material which is permeable to radiation X. Inside of the casing 40, a grid 42 for removing radiation X scattered from the patient 22, a radiation detection device 44 for detecting radiation X that has passed through the patient 22, and a lead plate 46 for absorbing backscattered radiation X are arranged in this order from the side which is irradiated with radiation X.

Figure 3:
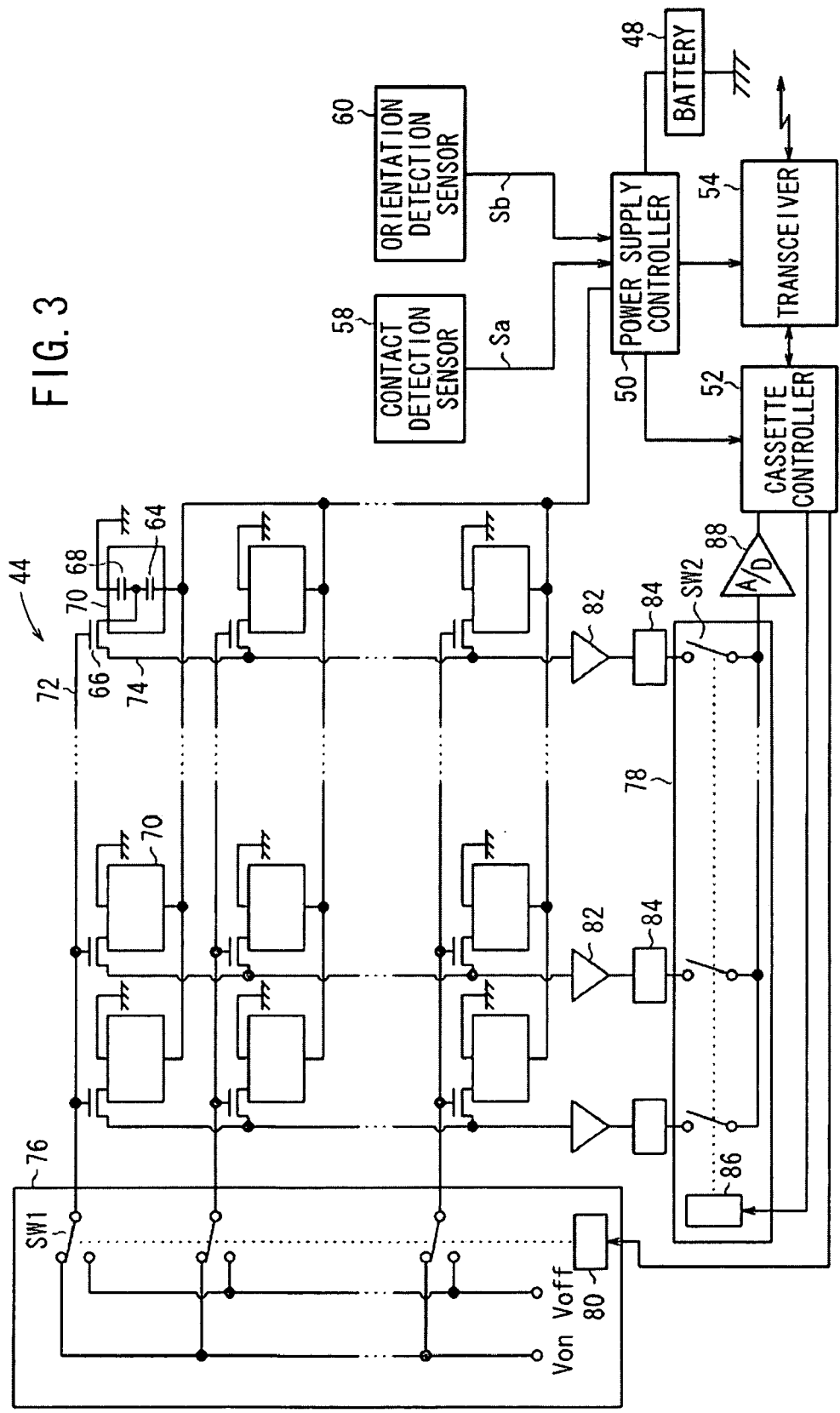
FIG. 3 is a schematic block diagram of a circuit structure of a radiation conversion device accommodated inside the electronic cassette.

Further, as shown in FIG. 3, a battery 48 which serves as a power source for the electronic cassette 28, a power supply controller 50 that controls supply of power from the battery 48, a cassette controller 52 that controls driving of the radiation detection device 44, and a transceiver 54 that transmits and receives signals including image information of the radiation detected by the radiation detection device 44, between the cradle 30, the portable information terminal 32 and the console 34, are accommodated in the casing 40. Moreover, in the cassette controller 52 and the transceiver 54, for avoiding damage caused by irradiation of radiation X, it is preferable for a lead plate or the like to be disposed on a surface side of the casing 40 that is subject to being irradiated with radiation X.

As shown in FIG. 2, a handle 56 is provided on one side surface of the casing 40 for enabling carrying and conveying of the electronic cassette 28 to an imaging position. On the handle 56, a contact detection sensor 58 is disposed for sensing that the handle 56 has been gripped by a technician. For the contact detection sensor 58, for example, a microswitch, a pressure sensor having therein a piezoelectric element, or the like, i.e., any small sized sensing switch for detecting an ON/OFF state may be used. Accordingly, when the handle 56 is gripped by a technician, the contact detection sensor 58 outputs a contact detection signal Sa (see FIG. 3). An optical sensor, an electrostatic sensor or the like may also be used as the contact detection sensor 58.

In addition, an orientation detection sensor 60 (see FIG. 3) is provided inside of the casing 40 for detecting that the casing 40 has been moved by the technician. For example, an angle sensor that detects a voltage change caused by movement of a ball made of a dielectric body, or a vibration gyro that detects a direction of vibration caused by self-vibration of a dielectric body, can be used as the orientation detection sensor 60.

Accordingly, as a result of the handle 56 of the casing 40 being gripped by a technician, and by carrying the electronic cassette 28, respective detection signals comprising a contact detection signal Sa and an orientation detection signal Sb are output from the contact detection sensor 58 and the orientation detection sensor 60.

Further, as shown in FIG. 2, a liquid crystal display unit 62 is provided on a side surface of the casing 40. At least a message, which indicates that the electronic cassette 28 cannot transition to an image capturing capable mode, is displayed on the liquid crystal display unit 62.

As shown in FIG. 3, the radiation detection device 44 includes a structure in which a photoelectric conversion layer 64 made up from an amorphous selenium (a-Se) material or the like, which generates electric charges upon sensing radiation X, is disposed on thin film transistors (TFTs) 66 arrayed in a matrix form. After the generated electric charges are accumulated in storage capacitors 68, the TFTs 66 are successively turned on one line at a time, and the electric charges are read out as image signals. FIG. 3 shows the connected relationship of only one of the TFTs 66 and one pixel (image element) 70 made up from a photoelectric conversion layer 64 and a storage capacitor 68, whereas the structures of other similar pixels 70 have been omitted from illustration for the sake of simplicity. Since when heated to high temperatures, the structure of amorphous selenium changes and the functionality thereof is lowered, amorphous selenium must be used within a prescribed temperature range. Accordingly, it is preferable to provide some means for cooling the radiation detection device 44 inside the electronic cassette 28.

Gate lines 72, which extend in parallel to the direction of the rows, and signal lines 74 which extend in parallel to the direction of the columns, are connected to the TFTs 66, which are connected respectively to each of the pixels 70. Each of the gate lines 72 is connected to a line scanning driver 76, and each of the signal lines 74 is connected to a multiplexer 78 that constitutes a reading circuit.

Control signals Von, Voff that control ON and OFF states of the TFTs 66 arrayed in the direction of the rows, are supplied from the line scanning driver 76 to the gate lines 72. In this case, the line scanning driver 76 comprises a plurality of switches SW1 that switch the gate lines 72 on or off, and a first address decoder 80, which outputs selection signals for selecting one of the switches SW1. Address signals are supplied from the cassette controller 52 to the first address decoder 80.

Further, the signal lines 74 are supplied with electric charges, which are stored in the storage capacitors 68 of each of the pixels 70, through the TFTs 66 arranged in the columns. The electric charges supplied to the signal lines 74 are amplified by amplifiers 82. The amplifiers 82 are connected through respective sample and hold circuits 84 to the multiplexer 78. The multiplexer 78 comprises a plurality of switches SW2 for successively switching between the signal lines 74, and a second address decoder 86 for outputting a selection signal for selecting one of the switches SW2 at a time. The second address decoder 86 is supplied with an address signal from the cassette controller 52. An A/D converter 88 is connected to the multiplexer 78. A radiation image signal is converted by the A/D converter 88 into a digital image signal representing the radiation image information, which is supplied to the cassette controller 52.

Further, inside the casing 40 of the electronic cassette 28, an image memory 89 is arranged, which stores the radiation image information detected by the radiation detection device 44. The radiation image information is transmitted through the transceiver 54 to the cradle 30, the portable information terminal 32 and the console 34. The radiation image information may be transmitted, if necessary, in a condition of being subjected to data compression.

Figure 4:
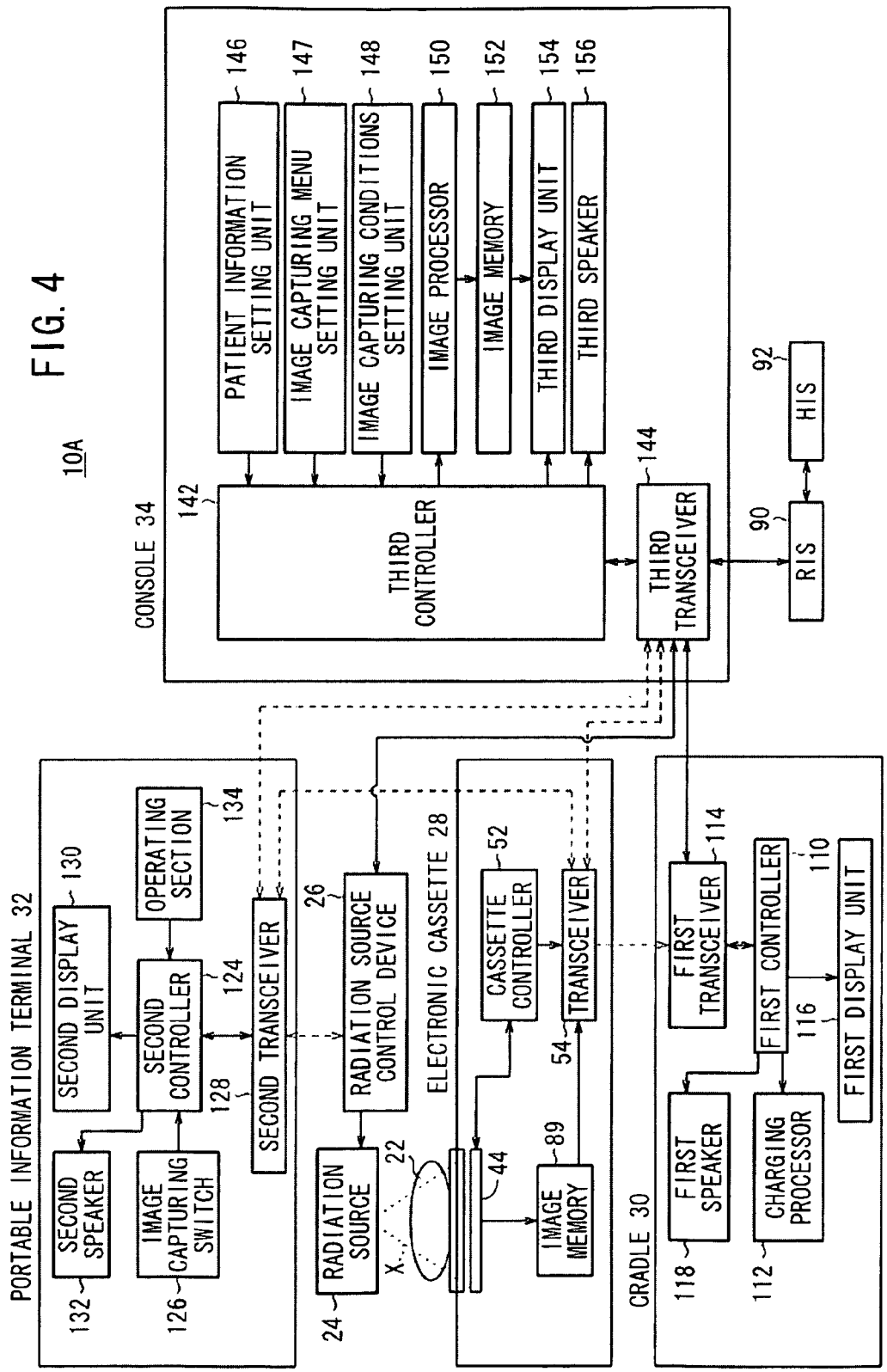
FIG. 4 is a schematic block diagram of the first radiation image capturing system.

FIG. 4 is a schematic block diagram of a first radiation image capturing system 10A. The console 34 is connected to a radiology information system (RIS) 90, which generally manages radiation image information handled by the radiological department of a hospital along with other information. The RIS 90 is connected to a hospital information system (HIS) 92, which generally manages medical information in the hospital.

Further, as shown in FIG. 3, the power supply controller 50 of the electronic cassette 28 supplies power to the cassette controller 52 and the transceiver 54 based on the contact detection signal Sa from the contact detection sensor 58 and the orientation detection signal Sb from the orientation detection sensor 60. When it is determined that the electronic cassette 28 can transition to the image capturing capable mode (in the case that a permission signal Sc is output from an image capturing capable mode discriminating unit 94, to be mentioned later), a control is performed to supply electrical power to the radiation detection device 44 and other electronic circuits.

Figure 5:
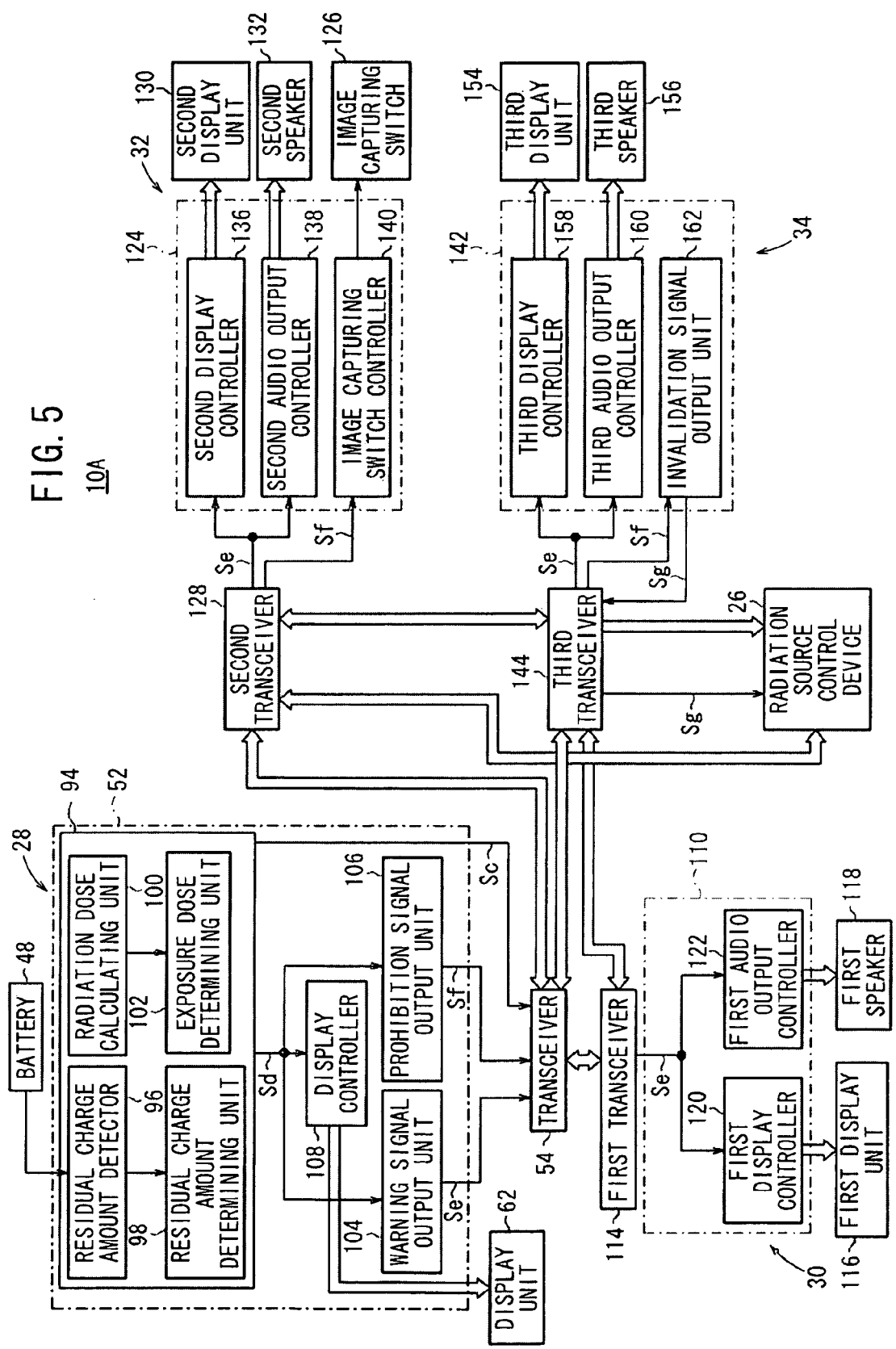
FIG. 5 is a schematic block diagram showing main components of each of the controllers of the first radiation image capturing system.

Additionally, as shown in FIG. 5, the cassette controller 52 of the electronic cassette 28 includes an image capturing capable mode discriminating unit 94, which determines whether or not the electronic cassette 28 can transition to the image capturing capable mode based on the power supply.

The image capturing capable mode discriminating unit 94 includes a residual charge amount detector 96 for detecting at least a residual charge amount of the battery 48, a residual charge amount determining unit 98 for determining whether or not the detected residual charge amount is equal to or greater than a predetermined amount (i.e., the power amount needed for a one time exposure to radiation), a radiation dose calculating unit 100 for calculating a cumulative exposure dose of the radiation detection device 44, and an exposure dose determining unit 102 for determining whether or not the calculated cumulative exposure dose has exceeded an acceptable amount.

In the case it is determined in the residual charge amount determining unit 98 that the residual charge amount is equal to or greater than the predetermined amount, and if it is determined in the exposure dose determining unit 102 that the cumulative exposure dose does not exceed the acceptable amount, then a permission signal Sc is output from the image capturing capable mode discriminating unit 94. On the other hand, if it is determined in the residual charge amount determining unit 98 that the residual charge amount is less than the predetermined amount, or if it is determined in the exposure dose determining unit 102 that the cumulative exposure dose exceeds an acceptable amount, then a non-permission signal Sd is output from the image capturing capable mode discriminating unit 94.

The cassette controller 52 further includes a warning signal output unit 104, a prohibition signal output unit 106, and a display controller 108.

The warning signal output unit 104 outputs a warning signal Se for issuing a warning based on output of the non-permission signal Sd, which is output from the image capturing capable mode discriminating unit 94. The prohibition signal output unit 106 outputs an exposure prohibition signal Sf for prohibiting output of radiation X from the radiation source 24, based on output of the non-permission signal Sd.

The above-mentioned permission signal Sc, warning signal Se, and exposure prohibition signal Sf are transmitted to an external device (for example, the portable information terminal 32, the cradle 30, the console 34, etc.) through the transceiver 54.

The display controller 108 carries out a control to display a message or mark (for example an NG mark), to indicate that the electronic cassette 28 cannot transition to the radiation capturing capable mode, on the display unit 62 disposed on the side surface of the casing 40, based on output of the non-permission signal Sd.

On the other hand, as shown in FIG. 4, a first controller 110 of the cradle 30 controls a charging processor 112 for carrying out a charging process on the battery 48 of the electronic cassette 28, whereas information received from the console 34 through a first transceiver 114 is displayed on a first display unit 116, together with causing a first speaker (audio output unit) 118 to emit sounds when necessary. Radiation image information acquired from the electronic cassette 28 may also be displayed as a preview image on the first display unit 116.

Further, as shown in FIG. 5, the first controller 110 of the cradle 30 includes a first display controller 120 and a first audio output controller 122. The first display controller 120 carries out a control to display a message or mark (for example an NG mark) on the first display unit 116, to indicate that the electronic cassette 28 cannot transition to the radiation capturing capable mode, based on input of the warning signal Se output from the electronic cassette 28. The first audio output controller 122 carries out a control to cause a warning sound to be output through the first speaker 118 based on input of the warning signal Se.

As shown in FIG. 4, a second controller 124 of the portable information terminal 32 supplies an image capturing signal, which is generated by the image capturing switch 126 that drives the radiation source 24, to the radiation source control device 26 through a second transceiver 128. Further, the second controller 124 displays information, received from the console 34 through the second transceiver 128, on a second display unit 130, while also causing a second speaker (audio output unit) 132 to emit sounds as necessary. Radiation image information acquired by the electronic cassette 28 may also be displayed as a preview image on the second display unit 130. Moreover, the portable information terminal 32 also includes an operating section 134, through which various necessary information can be set.

As shown in FIG. 5, the second controller 124 of the portable information terminal 32 includes a second display controller 136, a second audio output controller 138, and an image capturing switch controller 140. The second display controller 136 carries out a control to display a message or mark (for example an NG mark) on the second display unit 130, to indicate that the electronic cassette 28 cannot transition to the radiation capturing capable mode, based on input of the warning signal Se output from the electronic cassette 28. The second audio output controller 138 carries out a control to cause a warning sound to be output through the second speaker 132 based on input of the warning signal Se. The image capturing switch controller 140 temporarily invalidates operations of the image capturing switch 126 based on input of the exposure prohibition signal Sf, which is output from the electronic cassette 28, for example until a subsequent permission signal Sc arrives.

As shown in FIG. 4, the console 34 is equipped with a third controller 142, a third transceiver 144 for transmitting and receiving necessary information via wireless communications with respect to the radiation source control device 26, the electronic cassette 28, the cradle 30 and the portable information terminal 32, a patient information setting unit 146 for setting patient information, an image capturing menu setting unit 147 for selecting and setting an image capturing region of the patient 22 from an image capturing menu, an image capturing conditions setting unit 148 for setting required image capturing conditions for an image to be captured by the radiation source control device 26, an image processor 150 for performing image processing on the radiation image information, which is transmitted from the electronic cassette 28, an image memory 152 for storing the processed radiation image information, a third display unit 154 for displaying radiation image information, patient information, the image capturing menu and the like, and a third speaker (audio output unit) 156 for emitting a warning notice when necessary.

The patient information is defined as information for specifying a patient 22, such as the name and sex of the patient 22, a patient ID number, and the like. The image capturing menu serves as a menu for selecting an image capturing region of the patient 22. As an image capturing region, the head region, a chest region, or regions of the four limbs, etc., of the patient 22 may be considered. The image capturing conditions are conditions for determining a supplied tube voltage, tube current, irradiation time, etc., for irradiating an imaging region of the patient 22 with an appropriate dose of radiation X. Image capturing order information, including the patient information, the imaging capturing menu and the image capturing conditions, can be set directly by the console 34, or can be supplied externally to the console 34 through the RIS 90.

As shown in FIG. 5, the third controller 142 of the console 34 includes a third display controller 158, a third audio output controller 160, and an invalidation signal output unit 162. The third display controller 158 carries out a control to display a message or mark (for example an NG mark) on the third display unit 154, to indicate that the electronic cassette 28 cannot transition to the radiation capturing capable mode, based on input of the warning signal Se output from the electronic cassette 28. The third audio output controller 160 carries out a control to cause a warning sound to be output through the third speaker 156 based on input of the warning signal Se. The invalidation signal output unit 162 outputs an invalidation signal Sg to the radiation source control device 26 based on input of the exposure prohibition signal Sf, which is output from the electronic cassette 28. By inputting the invalidation signal Sg to the radiation source control device 26, input interruption from the portable information terminal 32 with respect to the radiation source control device 26 is temporarily prohibited.

The first radiation image capturing system 10A according to the present embodiment is constructed basically as described above. Next, explanations shall be made concerning operations of the first radiation image capturing system 10A.

When a radiation image of the patient 22 is to be captured, using the patient information setting unit 146 of the console 34, patient information concerning the patient 22 is set, together with setting required image capturing conditions using the image capturing conditions setting unit 148. Further, using the image capturing menu setting unit 147, a desired image capturing region, for example, the head region, a chest region, or a region of the four limbs, etc., is selected and set from the image capturing menu displayed on the third display unit 154.

The set patient information, image capturing conditions and image capturing region are transmitted to the portable information terminal 32 held by the technician and displayed on the second display unit 130 thereof. In this case, the technician confirms the patient information, the image capturing conditions and the image capturing region, which are displayed on the second display unit 130 of the portable information terminal 32, so that desired preparations for capturing the image can be carried out.

Next, for example, the technician selects one electronic cassette 28 from among a plurality of available electronic cassettes 28, and performs an operation to grip the handle 56 of the selected electronic cassette 28 and to lift up the electronic cassette 28. By gripping the handle 56, a contact detection signal Sa is output from the contact detection sensor 58, and further by lifting up the casing 40, an orientation detection signal Sb is output from the orientation detection sensor 60.

The power supply controller 50 supplies electrical power to the cassette controller 52 and the transceiver 54 based on input of the contact detection signal Sa and the orientation detection signal Sb.

Based on supply of power to the cassette controller 52, the image capturing capable mode discriminating unit 94 is initiated, whereupon first, it is determined in the residual charge amount determining unit 98 whether or not the residual charge amount of the battery 48 from the residual charge amount detector 96 is equal to or greater than a predetermined value (i.e., a power amount needed for one radiation exposure). Next, it is determined in the exposure dose determining unit 102 whether or not the cumulative exposure dose calculated by the radiation dose calculating unit 100 exceeds the acceptable amount.

If it is determined in the residual charge amount determining unit 98 that the residual charge amount is equal to or greater than the predetermined amount, and if it is determined in the exposure dose determining unit 102 that the cumulative exposure dose does not exceed the acceptable amount, then a permission signal Sc is output from the image capturing capable mode discriminating unit 94.

Conversely, if it is determined in the residual charge amount determining unit 98 that the residual charge amount is less than the predetermined amount, or if it is determined in the exposure dose determining unit 102 that the cumulative exposure dose exceeds the acceptable amount, then a non-permission signal Sd is output from the image capturing capable mode discriminating unit 94.

In addition, in the image capturing capable mode discriminating unit 94, in the case it is determined that the electronic cassette 28 can transition to the image capturing capable mode (that is, if the permission signal Sc is output from the image capturing capable mode discriminating unit 94), then the power supply controller 50 performs a control to supply electrical power to the radiation detection device 44 and to other electronic circuits.

On the other hand, in the case it is determined in the image capturing capable mode discriminating unit 94 that the electronic cassette 28 cannot transition to the image capturing capable mode (that is, if the non-permission signal Sd is output from the image capturing capable mode discriminating unit 94), then a warning signal Se is output from the warning signal output unit 104 of the cassette controller 52, and an exposure prohibition signal Sf is output from the prohibition signal output unit 106. The warning signal Se and the exposure prohibition signal Sf are transmitted through the transceiver 54 to the portable information terminal 32, the cradle 30 and the console 34.

Together therewith, a message or mark (for example an NG mark) is displayed on the display unit 62 that is arranged on the side surface of the casing 40 by the display controller 108 of the cassette controller 52, to indicate that the electronic cassette 28 cannot transition to the image capturing capable mode.

Accordingly, as a result of lifting up the electronic cassette 28 and observing the display unit 62 on the side surface of the casing 40, the technician can confirm easily whether the electronic cassette 28 has transitioned to an image capturing capable mode, or alternatively, whether the electronic cassette 28 cannot transition to the image capturing capable mode. In the event that the electronic cassette 28 cannot transition to the image capturing capable mode, the electronic cassette 28 can be replaced swiftly and easily with a different electronic cassette 28.

As described above, the warning signal Se and the exposure prohibition signal Sf, which are output from the electronic cassette 28, are input to the portable information terminal 32. In this case, a message or mark (for example an NG mark) is displayed on the second display unit 130 disposed on the portable information terminal 32, to indicate that the electronic cassette 28 cannot transition to the image capturing capable mode, while a warning is output audibly through the second speaker 132. Furthermore, by input of the exposure prohibition signal Sf, operation of the image capturing switch 126 is temporarily disabled (invalidated). A technician operating the portable information terminal 32 (who may be a different person from the technician who handles the electronic cassette 28), stops operation of the image capturing switch 126, by confirming the message displayed on the second display unit 130 together with the audibly output warning. Even if the image capturing switch 126 is still operated by mistake, since the switch is temporarily disabled, irradiation and exposure to X-rays cannot be performed.

Similarly, the warning signal Se output from the electronic cassette 28 is input to the cradle 30. In this case, a message or mark (for example an NG mark) is displayed also on the first display unit 116 provided on the cradle 30, to indicate that the electronic cassette 28 cannot transition to the image capturing capable mode, while a warning is output audibly through the first speaker 118. Owing thereto, a technician in the proximity of the cradle 30 also can confirm easily that the electronic cassette 28 cannot transition to the image capturing capable mode.

Further, the warning signal Se and the exposure prohibition signal Sf output from the electronic cassette 28 are input to the console 34. In this case, a message or mark (for example an NG mark) is displayed on the third display unit 154 of the console 34, to indicate that the electronic cassette 28 cannot transition to the image capturing capable mode, while a warning is output audibly through the third speaker 156. Further, in accordance with input of the exposure prohibition signal Sf, an invalidation signal Sg is output to the radiation source control device 26. By inputting the invalidation signal Sg to the radiation source control device 26, input interruption from the portable information terminal 32 with respect to the radiation source control device 26 is temporarily prohibited. Owing thereto, irradiation of X-rays can be temporarily stopped in a reliable manner. Given a specification in which the exposure prohibition signal Sf is not transmitted to the portable information terminal 32, this is made valid in the case that the electronic cassette 28 cannot transition to an image capturing capable mode.

In addition, in the case that the selected electronic cassette 28, or the electronic cassette 28 with which it was replaced, has transitioned to the image capturing capable mode, after the permission signal Sc has been output from the electronic cassette 28, ordinary operations are carried out with respect to the electronic cassette 28.

More specifically, first, the technician places the electronic cassette 28 on a desired image capturing region of the patient 22, as selected from the image capturing menu.

Once the electronic cassette 28 has been placed in an appropriate state with respect to the patient 22, the technician operates the image capturing switch 126 of the portable information terminal 32 in order to carry out capturing of the radiation image. When the image capturing switch 126 is operated, the second controller 124 of the portable information terminal 32 transmits an image capturing initiation signal to the radiation source control device 26 via the second transceiver 128. The radiation source control device 26, which has received the image capturing initiation signal, controls the radiation source 24 according to the image capturing conditions supplied beforehand from the console 34, and thereby irradiates the patient 22 with radiation X.

Radiation X that has passed through the patient 22, after scattered rays have been removed by the grid 42 of the electronic cassette 28, irradiate the radiation detection device 44 and are converted into electric signals by the photoelectric conversion layer 64 of each of the pixels 70 making up the radiation detection device 44, which are retained as charges in the storage capacitors 68 (see FIG. 3). Next, the electric charge information that forms the radiation image information of the patient 22 stored in each of the storage capacitors 68 is read out in accordance with address signals, which are supplied from the cassette controller 52 to the line scanning driver 76 and the multiplexer 78.

More specifically, the first address decoder 80 of the line scanning driver 76 outputs a selection signal based on the address signal supplied from the cassette controller 52, thereby selecting one of the switches SW1, and supplies a control signal Von to the gate of the TFT 66 that is connected to a corresponding gate line 72. On the other hand, the second address decoder 86 of the multiplexer 78 outputs a selection signal according to the address signal supplied from the cassette controller 52, and successively switches the switches SW2, whereby the radiation image information, which is formed as electric charge information stored in the storage capacitors 68 of each of the pixels (image elements) 70 that are connected to the gate line 72 selected by the line scanning driver 76, is read out in succession through the signal lines 74.

After the radiation image information read from the storage capacitors 68 of the pixels 70 connected to the selected gate line 72 of the radiation detection device 44 has been amplified by the respective amplifiers 82, the radiation image information is sampled by each of the sample and hold circuits 84, and supplied to the A/D converter 88 through the multiplexer 78 and converted into digital signals. The radiation image information having been converted into digital signals is temporarily stored in the image memory 89 connected to the cassette controller 52.

Similarly, the first address decoder 80 of the line scanning driver 76 successively turns on the switches SW1 according to the address signals supplied from the cassette controller 52, and reads out the radiation image information, which is made up of charge information stored in the storage capacitors 68 of each of the pixels 70 connected respectively to the gate lines 72 through the signal lines 74, whereupon the radiation image information is stored in the image memory 89 connected to the cassette controller 52 through the multiplexer 78 and the A/D converter 88.

The radiation image information stored in the image memory 89 is transmitted to the console 34 by wireless communications through the transceiver 54, and after image processing has been implemented thereon by the image processor 150, the radiation image information is stored in the image memory 152 in a state of association with the patient information. Next, the radiation image information stored in the image memory 152 is displayed on the third display unit 154.

On the other hand, after the radiation image information stored in the image memory 89 of the electronic cassette 28 is subjected to data compression processing by the cassette controller 52, the information is transmitted to the cradle 30 or the portable information terminal 32, where the information can be displayed as a compressed image on the first display unit 116 or the second display unit 130. The technician can thereby confirm the compressed image displayed on the first display unit 116 or the second display unit 130, and can make a determination as to whether repeating of the image capturing process (i.e., capturing another image) is required or not. Because the amount of information is reduced as a result of data compression, the radiation image information can be displayed quickly.

In the electronic cassette 28, for which an image capturing process of the radiation image information has been carried out, the battery 48 thereof is consumed. In this case, the electronic cassette 28 is loaded into the cradle 30 so that a charging process can be performed with respect to the battery 48 thereof.

In this manner, in the first radiation image capturing system 10A, by causing a transition to the image capturing capable mode at a stage when a technician lifts up an electronic cassette 28 (assuming a case in which the electronic cassette 28 is one that can transition to an image capturing capable mode), a state that enables image capturing is made available at all times, whereby the time from setting the electronic cassette 28 at a desired position to actually starting image capturing can be shortened.

Of course, transition to the image capturing capable mode at a stage when the electronic cassette 28 is lifted up by the technician may result in inconveniences in terms of power consumption. However, according to the present embodiment, at the stage when the electronic cassette 28 is lifted up by the technician, supply of power is not carried out with respect to all of the electronic circuits including the radiation detection device 44. Rather, power initially is supplied to the cassette controller 52 and the transceiver 54, and at a stage when it is determined that the electronic cassette 28 can transition to the image capturing capable mode, supply of power is then carried out with respect to all of the electronic circuits including the radiation detection device 44. Therefore, electrical power consumption can effectively be reduced.

Further, in the case that the electronic cassette 28 cannot transition to the image capturing capable mode at a stage when the electronic cassette 28 is lifted by the technician, by issuing a warning, the time required to replace the electronic cassette 28 with a different electronic cassette 28 can be shortened, and thus operations for capturing a radiation image utilizing electronic cassettes 28 can be carried out more swiftly.

Further, at a stage when the electronic cassette 28 is lifted, in the case that the electronic cassette 28 cannot transition to the image capturing capable mode, since exposure to radiation can be temporarily prohibited, needless exposure to radiation can be prevented. Thus, consideration and care can be realized with respect to exposing the patient to undue radiation, and the useful life of the electronic, cassette 28 can be prolonged. Even though exposure to radiation is temporarily stopped, the situation is resolved only in the time required for the technician to replace the electronic cassette 28 with another one, thereby eliminating any undue psychological burden imposed on the patient.

Next, a number of modified examples of the first radiation image capturing system 10A shall be explained.

Figure 6:
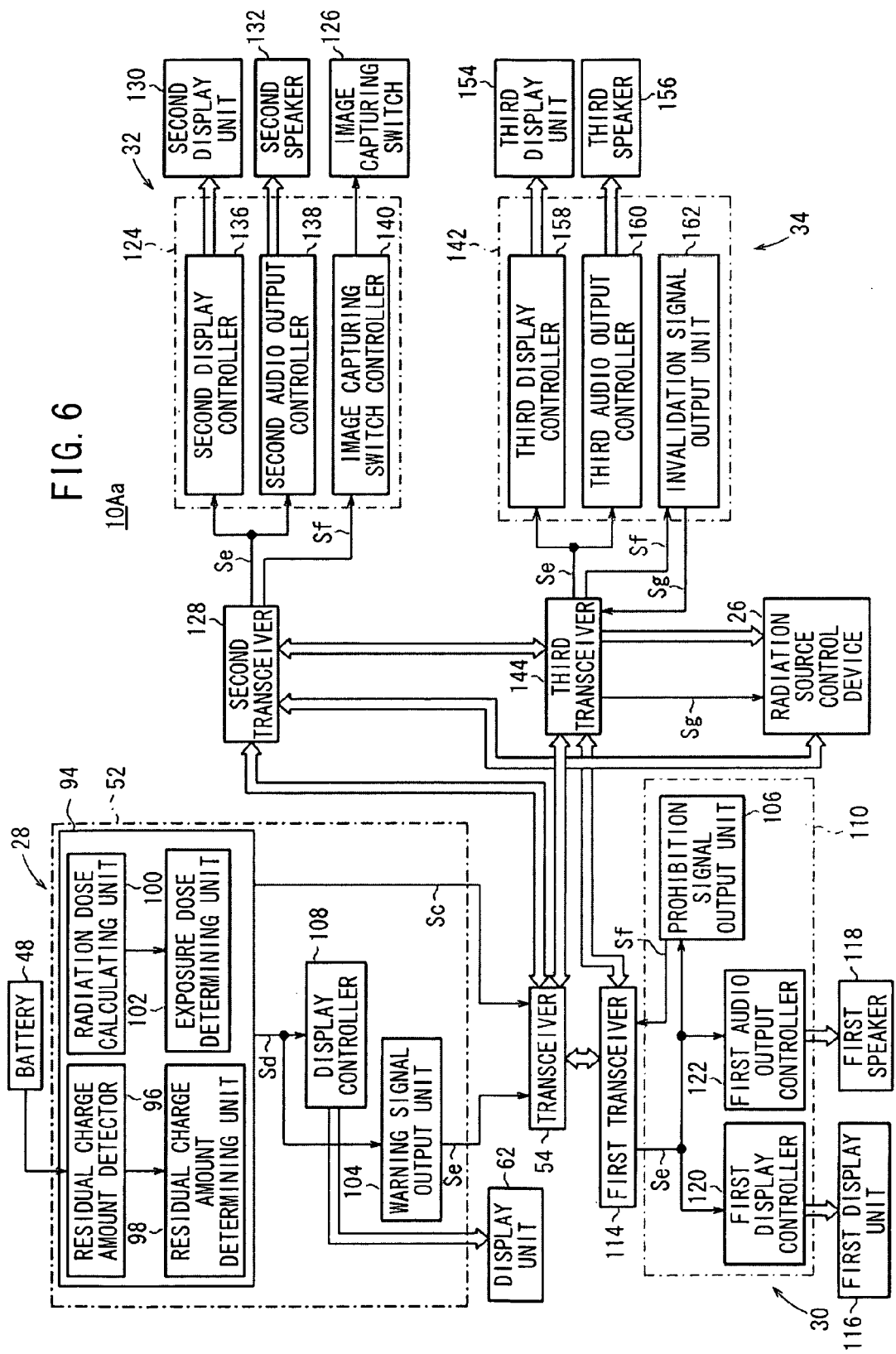
FIG. 6 is a schematic block diagram showing principal components of each of the controllers, in accordance with a first modified example of the first radiation image capturing system.
Figure 7:
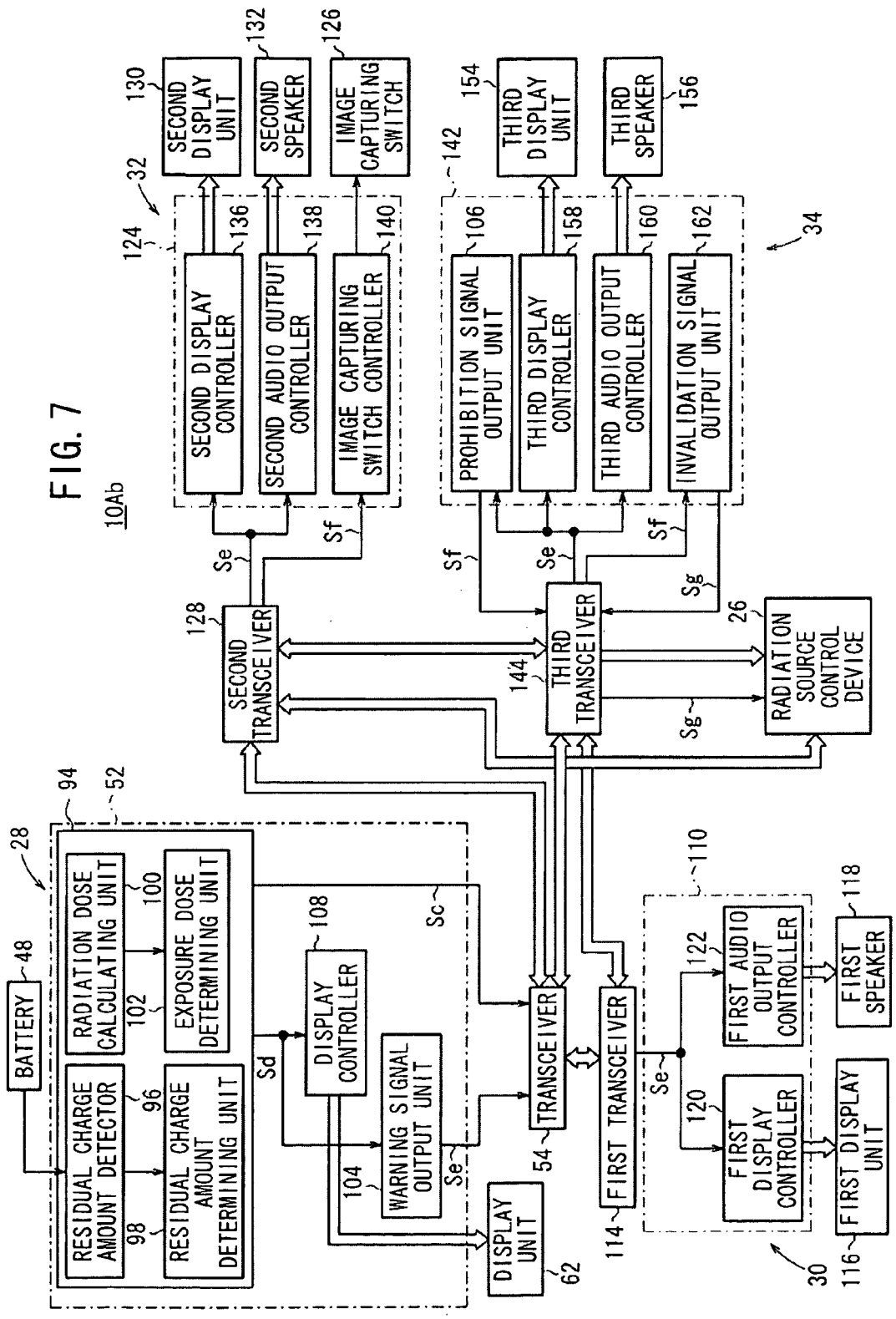
FIG. 7 is a schematic block diagram showing principal components of each of the controllers, in accordance with a second modified example of the first radiation image capturing system.

Initially, a radiation image capturing system 10Aa according to a first modified example has substantially the same structure as the aforementioned first radiation image capturing system 10A. However, as shown in FIG. 6, the radiation image capturing system 10Aa differs in that the prohibition signal output unit 106 is not included in the cassette controller 52 of the electronic cassette 28, but rather is incorporated into the first controller 110 of the cradle 30.

In this case, the prohibition signal output unit 106 inside the cradle 30 outputs an exposure prohibition signal Sf based on input of the warning signal Se, which is output from the electronic cassette 28. The exposure prohibition signal Sf is transmitted to the portable information terminal 32 and the console 34 through the first transceiver 114.

A radiation image capturing system 10Ab according to a second modified example has substantially the same configuration as the first radiation image capturing system 10A, but differs therefrom in that the prohibition signal output unit 106 is not included in the cassette controller 52 of the electronic cassette 28, but rather is incorporated into the third controller 142 of the console 34.

In this case, the prohibition signal output unit 106 inside the console 34 outputs an exposure prohibition signal Sf based on input of the warning signal Se, which is output from the electronic cassette 28. The exposure prohibition signal Sf is transmitted to the portable information terminal 32 through the third transceiver 144.

Next, a radiation image capturing system according to a second embodiment (hereinafter, referred to as a second radiation image capturing system 10B) shall be described below with reference to FIG. 8.

As shown in FIG. 8, the second radiation image capturing system 10B has substantially the same configuration as the aforementioned first radiation image capturing system 10A, but differs therefrom in the following features.

More specifically, the cassette controller 52 includes a timer initiation signal output unit 164, a normal operation signal output unit 166, a timer 168, a prohibition signal output unit 106, and a display controller 108.

The timer initiation signal output unit 164 outputs a timer initiation signal Sh based on input thereto of the contact detection signal Sa and the orientation detection signal Sb.

The normal operation signal output unit 166 outputs a normal operations signal Si, which indicates that the electronic cassette 28 has transitioned to the image capturing capable mode, based on output of the permission signal Sc from the image capturing capable mode discriminating unit 94.

The prohibition signal output unit 106 outputs an exposure prohibition signal Sf, in the event that the normal operation signal Si from the normal operation signal output unit 166 is not input within a predetermined time period from a time of input of the timer initiation signal Sh that is output from the timer initiation signal output unit 164. The predetermined time period is obtained by counting clock pulses from the timer 168. The timer initiation signal Sh, the normal operation signal Si and the exposure prohibition signal Sf are transmitted to the portable information terminal 32, the cradle 30 and the console 34 through the transceiver 54.

In the event that the normal operation signal Si is not input within the predetermined time period from a time of input of the timer initiation signal Sh, the display controller 108 performs a control so that a message or mark (for example an NG mark) is displayed on the display unit 62 disposed on the side surface of the casing 40, to indicate that the electronic cassette 28 cannot transition to the image capturing capable mode.

The first controller 110 of the cradle 30 includes a first display controller 120, a first audio output controller 122, and a first timer 170.

In the event that the normal operation signal Si from the electronic cassette 28 is not input within the predetermined time period from a time of input of the timer initiation signal Sh that is output from the electronic cassette 28, the first display controller 120 performs a control so that a message or mark (for example an NG mark) is displayed on the first display unit 116 of the cradle 30, to indicate that the electronic cassette 28 cannot transition to the image capturing capable mode. In this case, the predetermined time period is obtained by counting clock pulses from the first timer 170.

In the event that the normal operation signal Si is not input within the predetermined time period from the time of input of the timer initiation signal Sh, the first audio output controller 122 performs a control to audibly output a warning through the first speaker 118.

The second controller 124 of the portable information terminal 32 includes a second display controller 136, a second audio output controller 138, an image capturing switch controller 140, and a second timer 172.

In the event that the normal operation signal Si from the electronic cassette 28 is not input within a predetermined time period from the time of input of the timer initiation signal Sh that is output from the electronic cassette 28, the second display controller 136 performs a control so that a message or mark (for example, an NG mark) is displayed on the second display unit 130 of the portable information terminal 32, to indicate that the electronic cassette 28 cannot transition to the image capturing capable mode.

In the event that the normal operation signal Si is not input within the predetermined time period from the time of input of the timer initiation signal Sh, the second audio output controller 138 performs a control to audibly output a warning through the second speaker 132.

Based on the exposure prohibition signal Sf output from the electronic cassette 28, the image capturing switch controller 140 performs a control to invalidate operation of the image capturing switch 126 temporarily, for example, until arrival of the normal operation signal Si.

The third controller 142 of the console 34 includes a third display controller 158, a third audio output controller 160, an invalidation signal output unit 162, and a third timer 174.

In the case that the normal operation signal Si from the electronic cassette 28 is not input within a predetermined time period from a time of input of the timer initiation signal Sh that is output from the electronic cassette 28, the third display controller 158 performs a control so that a message or mark (for example an NG mark) is displayed on the third display unit 154 of the console 34, to indicate that the electronic cassette 28 cannot transition to the image capturing capable mode.

The third audio output controller 160 controls the third speaker 156 so as to output an audio warning in the event that the normal operation signal Si is not input within a predetermined time period from the point when the timer initiation signal Sh has been input.

The invalidation signal output unit 162 outputs an invalidation signal Sg to the radiation source control device 26 based on input of the exposure prohibition signal Sf, which is output from the electronic cassette 28. By inputting the invalidation signal Sg to the radiation source control device 26, input interruption from the portable information terminal 32 with respect to the radiation source control device 26 is temporarily prohibited.

In the second radiation image capturing system 10B as well, substantially the same effects and advantages of the aforementioned first radiation image capturing system 10A can be obtained.

Further, in the second radiation image capturing system 10B as well, structures analogous to the aforementioned radiation image capturing system 10Aa according to the first modified example, or the radiation image capturing system 10Ab according to the second modified example, can be adopted in a similar manner.

Of course, the present invention is not limited to the above-described embodiments, and the invention can be freely modified, within a range that does not deviate from the essence and gist of the present invention.

For example, the radiation detection device 44 accommodated in the electronic cassette 28 converts the radiation dose of the irradiated radiation X directly into electric signals through the photoelectric conversion layer 64 (direct conversion type). However, in place of this structure, a radiation detection device (indirect conversion type) in which irradiated radiation X is converted initially into visible light by a scintillator, and thereafter, the visible light is converted into electric signals using a solid-state detector element formed from amorphous silicon (a-Si) or the like, may also be used (see, Japanese Patent No. 3494683).

Further, the radiation image information can be obtained using a radiation detection device of light readout type. With such a light readout type of radiation detection device, radiation is irradiated onto respective solid state detection elements arranged in a matrix form, and an electrostatic latent image corresponding to the irradiation dose is stored cumulatively in the solid state detection elements. When the electrostatic latent image is read, reading light is irradiated onto the radiation detection device, and the generated current values are acquired as radiation image information. Further, by irradiating the radiation detection device with erasing light, the radiation image information in the form of a residual electrostatic latent image can be erased and the radiation detection device can be reused (see, Japanese Laid-Open Patent Publication No. 2000-105297).

Furthermore, a stimulable phosphor panel can also be used as the radiation detection device 44.

What is claimed is:

1. A radiation detection apparatus including a casing, radiation detection device accommodated inside the casing, which detects radiation emitted from a radiation source and having passed through a subject, and converts the radiation into radiation image information, and a radiation detection device controller that controls driving of at least the radiation detection device, further comprising:
    a sensor for sensing that the casing has been lifted;
    a power supply controller for supplying power at least to the radiation detection device controller based on a detection signal, which indicates that the casing has been lifted, from the sensor;
    a discriminating unit for discriminating whether the radiation detection apparatus has transitioned to an image capturing capable mode based on the power supply by the power supply controller; and
    a warning signal output unit for outputting a warning signal, for issuing a warning in the event that the radiation detection apparatus cannot transition to the image capturing capable mode.

2. The radiation detection apparatus according to claim 1, further comprising:
    a display unit provided on the casing; and
    a display controller for performing display of a warning on the display unit in the event that the radiation detection apparatus cannot transition to the image capturing capable mode.

3. The radiation detection apparatus according to claim 1, further comprising a prohibition signal output unit which outputs an exposure prohibition signal for prohibiting output of the radiation from the radiation source in the event that the radiation detection apparatus cannot transition to the image capturing capable mode.

4. A radiation detection apparatus including a casing, radiation detection device accommodated inside the casing, which detects radiation emitted from a radiation source and having passed through a subject, and converts the radiation into radiation image information, and a radiation detection device controller that controls driving of at least the radiation detection device, further comprising:
    a sensor for sensing that the casing has been lifted;
    a power supply controller for supplying power at least to the radiation detection device controller based on a detection signal, which indicates that the casing has been lifted, from the sensor;
    a discriminating unit for discriminating whether the radiation detection apparatus has transitioned to an image capturing capable mode based on the power supply by the power supply controller; and
    a normal operation signal output unit for outputting a normal operation signal indicating that the radiation detection apparatus has transitioned to the image capturing capable mode when the radiation detection apparatus has transitioned to the image capturing capable mode.

5. The radiation detection apparatus according to claim 4, further comprising:
    a display unit provided on the casing; and
    a display controller for performing display of a warning on the display unit in the case that the normal operation signal has not been output from the normal operation signal output unit even after a predetermined time period has elapsed from the output of the detection signal from the sensor.

6. The radiation detection apparatus according to claim 4, further comprising a prohibition signal output unit which outputs an exposure prohibition signal for prohibiting output of the radiation from the radiation source in the case that the normal operation signal has not been output from the normal operation signal output unit even after a predetermined time period has elapsed from the output of the detection signal from the sensor.

7. A radiation image capturing system, comprising:
    a radiation detection apparatus including a casing, a radiation detection device accommodated inside the casing, which detects radiation emitted from a radiation source and having passed through a subject, and converts the radiation into radiation image information, a radiation detection device controller that controls driving of at least the radiation detection device, and a battery; and
    a cradle for carrying out charging with respect to at least the battery by mounting the radiation detection apparatus into the cradle,
    wherein the radiation detection apparatus comprises:
    a sensor for sensing that the casing has been lifted;
    a power supply controller for supplying power at least to the radiation detection device controller based on a detection signal, which indicates that the casing has been lifted, from the sensor;
    a discriminating unit for discriminating whether the radiation detection apparatus has transitioned to an image capturing capable mode based on the power supply by the power supply controller; and
    a warning signal output unit for outputting a warning signal, for issuing a warning in the event that the radiation detection apparatus cannot transition to the image capturing capable mode; and
    wherein the cradle comprises:
    a warning output unit for issuing a warning based on input of the warning signal output from the warning signal output unit of the radiation detection apparatus.

8. The radiation image capturing system according to claim 7, wherein the warning output unit comprises:
    a display unit; and
    a display controller for performing display of a warning on the display unit based on input of the warning signal.

9. The radiation image capturing system according to claim 7, wherein the warning output unit comprises:
    an audio output unit;
    an audio output controller for controlling an audio output of a warning through the audio output unit based on input of the warning signal.

10. The radiation image capturing system according to claim 7, wherein the cradle comprises a prohibition signal output unit which outputs an exposure prohibition signal for prohibiting output of the radiation from the radiation source based on input of the warning signal.

11. A radiation image capturing system, comprising:
    a radiation detection apparatus including a casing, a radiation detection device accommodated inside the casing, which detects radiation emitted from a radiation source and having passed through a subject, and converts the radiation into radiation image information, a radiation detection device controller that controls driving of at least the radiation detection device, and a battery; and
    a cradle for carrying out charging with respect to at least the battery by mounting the radiation detection apparatus into the cradle, wherein the radiation detection apparatus comprises:
a sensor for sensing that the casing has been lifted;
a power supply controller for supplying power at least to the radiation detection device controller based on a detection signal, which indicates that the casing has been lifted, from the sensor;
a discriminating unit for discriminating whether the radiation detection apparatus has transitioned to an image capturing capable mode based on the power supply by the power supply controller; and
a normal operation signal output unit for outputting a normal operation signal indicating that the radiation detection apparatus has transitioned to the image capturing capable mode when the radiation detection apparatus has transitioned to the image capturing capable mode; and
wherein the cradle comprises:
a warning output unit for issuing a warning in the case that the normal operation signal has not been input from the normal operation signal output unit even after a predetermined time period has elapsed from the output of the detection signal from the sensor.

12. The radiation image capturing system according to claim 11, wherein the warning output unit comprises:
a display unit; and
a display controller for performing display of a warning on the display unit.

13. The radiation image capturing system according to claim 11, wherein the warning output unit comprises:
an audio output unit; and
an audio output controller for controlling an audio output of a warning through the audio output unit.

14. The radiation image capturing system according to claim 11, wherein the cradle comprises a prohibition signal output unit which outputs an exposure prohibition signal for prohibiting output of the radiation from the radiation source in the case that the normal operation signal has not been input from the normal operation signal output unit even after a predetermined time period has elapsed from the output of the detection signal from the sensor.

15. A radiation image capturing system, comprising:
a radiation detection apparatus including a casing, and a radiation detection device accommodated inside the casing, which detects radiation having passed through a subject, and converts the radiation into radiation image information, and a radiation detection device controller that controls driving of at least the radiation detection device;
an image capturing apparatus for irradiating the subject with radiation; and
a controller for controlling at least the image capturing apparatus by carrying out exchange of information with the radiation detection apparatus,
wherein the radiation detection apparatus comprises:
a sensor for sensing that the casing has been lifted;
a power supply controller for supplying power at least to the radiation detection device controller based on a detection signal, which indicates that the casing has been lifted, from the sensor;
a discriminating unit for discriminating whether the radiation detection apparatus has transitioned to an image capturing capable mode based on the power supply by the power supply controller; and
a warning signal output unit for outputting a warning signal, for issuing a warning in the event that the radiation detection apparatus cannot transition to the image capturing capable mode; and wherein the controller comprises:
a warning output unit for issuing a warning based on input of the warning signal output from the warning signal output unit of the radiation detection apparatus.

16. The radiation image capturing system according to claim 15, wherein the warning output unit comprises:
a display unit; and
a display controller for performing display of a warning on the display unit of the controller based on input of the warning signal.

17. The radiation image capturing system according to claim 15, wherein the warning output unit comprises:
an audio output unit;
an audio output controller for controlling an audio output of a warning through the audio output unit based on input of the warning signal.

18. The radiation image capturing system according to claim 15, wherein the radiation detection apparatus further comprises:
a prohibition signal output unit which outputs an exposure prohibition signal for prohibiting output of the radiation from the radiation source in the event that the radiation detection apparatus cannot transition to the image capturing capable mode; and
wherein the controller further comprises:
an invalidation signal output unit for outputting an invalidation signal for invalidating an image capturing instruction with respect to the image capturing apparatus, based on input of the exposure prohibition signal.

19. A radiation image capturing system, comprising:
a radiation detection apparatus including a casing, a radiation detection device accommodated inside the casing, which detects radiation having passed through a subject, and converts the radiation into radiation image information, and a radiation detection device controller that controls driving of at least the radiation detection device;
an image capturing apparatus for irradiating the subject with radiation; and
a controller for controlling at least the image capturing apparatus by carrying out exchange of information with the radiation detection apparatus,
wherein the radiation detection apparatus comprises:
a sensor for sensing that the casing has been lifted;
a power supply controller for supplying power at least to the radiation detection device controller based on a detection signal, which indicates that the casing has been lifted, from the sensor;
a discriminating unit for discriminating whether the radiation detection apparatus has transitioned to an image capturing capable mode based on the power supply by the power supply controller; and
a normal operation signal output unit for outputting a normal operation signal indicating that the radiation detection apparatus has transitioned to the image capturing capable mode, when the radiation detection apparatus has transitioned to the image capturing capable mode; and
wherein the controller comprises:
a warning output unit for issuing a warning in the case that the normal operation signal has not been input from the normal operation signal output unit even after a predetermined time period has elapsed from the output of the detection signal from the sensor.

20. The radiation image capturing system according to claim 19, wherein the warning output unit comprises:
a display unit; and a display controller for performing display of a warning on the display unit.

21. The radiation image capturing system according to claim 19, wherein the warning output unit comprises:
an audio output unit; and
an audio output controller for controlling an audio output of a warning through the audio output unit.

22. The radiation image capturing system according to claim 19, wherein the radiation detection apparatus further comprises:
a prohibition signal output unit which outputs an exposure prohibition signal or prohibiting output of the radiation from the radiation source, in the case that the normal operation signal has not been output from the normal operation signal output unit even after a predetermined time period has elapsed from the output of the detection signal from the sensor; and
wherein the controller further comprises:
an invalidation signal output unit for outputting an invalidation signal for invalidating an image capturing instruction with respect to the image capturing apparatus, based on input of the exposure prohibition signal.

* * * * *